United States Patent
Baughman et al.

(10) Patent No.: US 9,891,884 B1
(45) Date of Patent: Feb. 13, 2018

(54) AUGMENTED REALITY ENABLED RESPONSE MODIFICATION

(71) Applicant: International Business Machines Corporation, Armonk, NY (US)

(72) Inventors: Aaron K. Baughman, Silver Spring, MD (US); Nicholas A. McCrory, Sacramento, CA (US); Diwesh Pandey, Bangalore (IN); Rohit Pandey, Bangalore (IN)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 15/417,337

(22) Filed: Jan. 27, 2017

(51) Int. Cl.
  *G06F 17/00* (2006.01)
  *G06F 3/16* (2006.01)
  *G06K 9/00* (2006.01)

(52) U.S. Cl.
  CPC ......... *G06F 3/165* (2013.01); *G06K 9/00302* (2013.01)

(58) Field of Classification Search
  CPC ..................................................... G06F 3/165
  See application file for complete search history.

(56) References Cited

U.S. PATENT DOCUMENTS

| | | | |
|---|---|---|---|
| 8,831,255 | B2 | 9/2014 | Crawford et al. |
| 9,285,871 | B2 | 3/2016 | Geisner et al. |
| 2005/0208457 | A1 | 9/2005 | Fink et al. |
| 2011/0221669 | A1 | 9/2011 | Shams et al. |
| 2011/0221672 | A1 | 9/2011 | Osterhout et al. |
| 2011/0231757 | A1 | 9/2011 | Haddick et al. |
| 2013/0236040 | A1* | 9/2013 | Crawford ............... H04S 7/304 381/310 |
| 2014/0224099 | A1 | 8/2014 | Webman |
| 2015/0025662 | A1* | 1/2015 | Di Censo ............... G06F 3/011 700/94 |
| 2015/0195641 | A1 | 7/2015 | Di Censo et al. |
| 2015/0325047 | A1 | 11/2015 | Conner et al. |
| 2016/0149547 | A1 | 5/2016 | Rider et al. |
| 2016/0277850 | A1 | 9/2016 | Li et al. |

(Continued)

OTHER PUBLICATIONS

Albrecht et al., "A Mobile Augmented Reality Audio System with Binaural Microphones", IWS '11, Aug. 30, 2011, Stockholm, Sweden, pp. 7-11.

(Continued)

*Primary Examiner* — Joseph Saunders, Jr.
(74) *Attorney, Agent, or Firm* — David B. Woycechowsky

(57) ABSTRACT

A method for performing the following operations (not necessarily in the following order): (i) receiving by an augmented reality system, a series of images corresponding to views of the real world; (ii) processing, by the augmented reality system, the series of images to determine presence of a first object; (iii) determining, by the augmented reality system, that the first object meets a first set of conditions such that the first object belongs to a first object category; and (iv) responsive to the determination that the first object belongs to the first object category, providing an audio response in the form of one at least one of the following types of audio responses: communicating a predefined sound to an augmented reality user and/or changing audio characteristic(s) of a sound not generated by the augmented reality system which is being experienced by the augmented reality user.

12 Claims, 6 Drawing Sheets

(56) References Cited

U.S. PATENT DOCUMENTS

2016/0277863 A1 9/2016 Cahill et al.
2016/0332059 A1 11/2016 Seeff

OTHER PUBLICATIONS

Bordegoni et al., "Sound and Tangible Interface for shape Evaluation and Modification", HAVE 2008—IEEE International Workshop on Haptic Audio Visual Environments and their Applications, Ottawa, Canada, Oct. 18-19, 2008, 6 pages.

Delerue et al., "Mixage Mobile", IHM 2006, Montréal, Apr. 18-21, 2006, pp. 75-82.

Harma et al., "Augmented Reality Audio for Mobile and Wearable Appliances*", *Manuscript received Aug. 6, 2003; revised Jan. 26 and Mar. 15, 2004, J. Audio Eng. Soc., vol. 52, No. 6, Jun. 2004, pp. 618-639.

Kalantari et al., "Using Semantic Web Approach in Augmented Audio Reality System for Museum Visitors", Copyright is held by the author/owner(s), WWW 2004, May 17-22, 2004, New York, New York, USA, pp. 386-387.

Luo et al., "An Augmented Reality Training Environment for Post-Stroke Finger Extension Rehabilitation", Proceedings of the 2005 IEEE 9th International Conference on Rehabilitation Robotics, Jun. 28-Jul. 1, 2005, Chicago, IL, USA, pp. 329-332.

Pugliese et al., "ATSI: Augmented and Tangible Sonic Interaction Put a sound on it!", Making Connections, TEI 2015, Jan. 15-19, 2015, Stanford, CA, USA, pp. 97-104.

Rozier et al., "Here & There: An Augmented Reality System of Linked Audio", Sociable Media Group, MIT Media Lab, 20 Ames st., Cambridge, MA, USA, 6 pages, provided in Main Idea of Disclosure dated Feb. 8, 2016.

Trail et al., "The Wiikembe—A performer designed lamellophone hyperinstrument for idiomatic musical-DSP interaction", PACRIM'13, Aug. 27-29, 2013, University of Victoria, B.C., Canada, pp. 410-414.

* cited by examiner

AUGMENTED REALITY ENABLED RESPONSE MODIFICATION

BACKGROUND OF THE INVENTION

The present invention relates generally to the use of augmented reality techniques, and more specifically to augmented reality sound and audio.

The detection of particular sounds is known to produce responses. Some responses may be mild, whereas other response may be more extreme. In some instances, a particular sound is associated with a particular object. For example, a rattle snake is associated with a particular rattling sound. Some sounds and objects may have very strong associations such that independently viewing the object or hearing the sound may produce a given response.

Sound is generated by the vibrations of physical objects and the cascading effect of those vibrations in the surrounding mediums, which include gases, liquids, and solids that are in contact with the vibrating object. The vibrations of the physical objects can provide information regarding the attributes of those objects, such as texture, moisture, and distance between objects. From a human sound processing perspective, sound waves enter the outer ear and travel through the external auditory canal. The sound waves then reach the tympanic membrane of the ear, or eardrum, which in turn vibrates. This vibration of the eardrum moves the tiny chain of bones—malleus, incus, stapes—in the middle ear. The stapes then vibrates the Cochlea, which converts the displacement wave pulses into electric action potentials in the auditory nerve. As a result, certain sounds can evoke thought patterns and neurophysiological changes, which can have either a positive or negative effect on the emotional state of the recipient.

SUMMARY

According to an aspect of the present invention, there is a method, computer program product and/or computer system for performing the following operations (not necessarily in the following order): (i) receiving by an augmented reality system, a series of images corresponding to views of the real world; (ii) processing, by the augmented reality system, the series of images to determine presence of a first object; (iii) determining, by the augmented reality system, that the first object meets a first set of conditions such that the first object belongs to a first object category; and (iv) responsive to the determination that the first object belongs to the first object category, providing an audio response in the form of one at least one of the following types of audio responses: communicating a predefined sound to an augmented reality user and/or changing audio characteristic(s) of a sound not generated by the augmented reality system which is being experienced by the augmented reality user.

DETAILED DESCRIPTION

Figure 1:
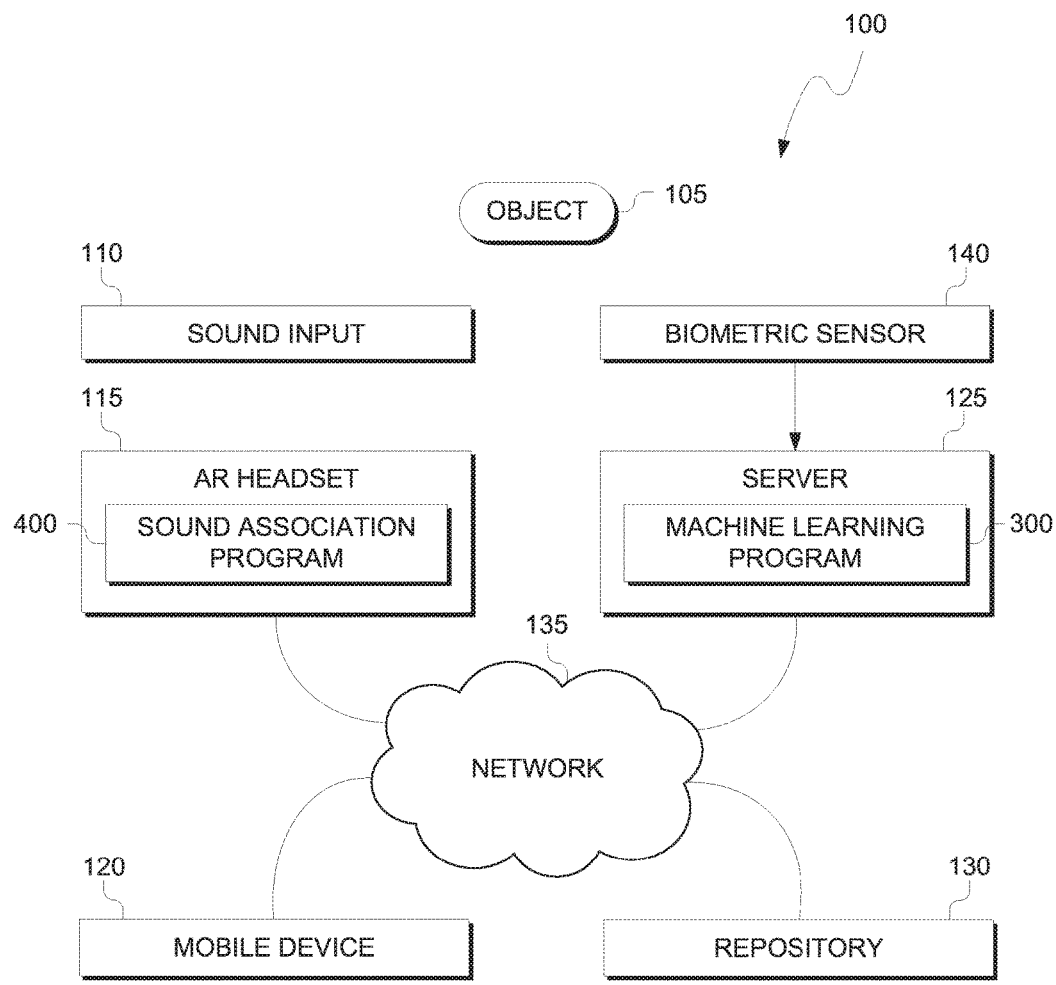
FIG. 1 is a functional block diagram illustrating a distributed computer processing environment applying augmented reality techniques, in accordance with an embodiment of the present invention.

The DETAILED DESCRIPTION section will be divided into the following sub-sections: (i) Glossary of Terms and Explanations; (ii) Introduction; and (iii) Embodiments of the Present Invention.

I. Glossary of Terms and Explanations

"User": refers to any living organism that is capable of using and appreciating embodiments of the present invention. For example, a user can be a human being or a chimpanzee that is capable of experiencing an emotional response.

"Stimulus" or "given stimulus": refers to a natural or non-natural input sound that is associated with a given physical object, or a digital or non-digital representation of a physical object. For example, a stimulus can include a physical object such a framed painting on a wall, or a digital image of the framed painting on a wall.

"Response" or "user response": refers to the emotional or psychological state of mind that a user is experiencing upon being exposed to a stimulus. For example, a user response can include fear, elation, or sadness.

"S/R association": S/R association refers to a Stimulus with a corresponding Response. For example, a Stimulus (S1) with a corresponding Response (R1) is an "S/R association," and can be represented as S1/R1.

"S/R pair": refers to a group of two S/R associations. For example, a group containing S1/R1 association and S2/R2 association, constitutes an "S/R pair."

"S/R set": refers to either at least one S/R pair or zero S/R pairs (empty S/R set). For example, a set containing S1/R1, S2/R2, S3/R3, and S4/R4 constitutes an S/R set. Additionally, a set containing zero S/R pairs constitutes an S/R set.

"And/or": non-exclusive or; for example, A and/or B means that: (i) A is true and B is false; or (ii) A is false and B is true; or (iii) A and B are both true.

"Include": contains all of aspects of the preceding object or process, but is not necessarily limited to the all aspects of the preceding object or process. For example, if object A includes elements B, C, and D, object A must contain elements B, C, and D, but is not necessarily limited to those elements.

II. Introduction

Real-world activity provides for a rich experience in which context can dictate perception, ranging from depth perception of an object or shaping an opinion on a particular subject matter. Having the ability to change or modify the context provides for an opportunity to change a user's experience. One approach by which a user may change the context is through the application of sound modification or augmentation in response to object recognition and/or sound detection associated with a particular user response, determined by machine learning. Augmented reality is a live view of a physical, real-world environment whose elements are augmented (or supplemented) by computer-generated sensory input such as sound, video, graphics, text, or Global Positioning System ("GPS") data, for example. More specifically, augmented reality sound can modify a user's response to detected objects and/or sounds, which can amplify or mitigate a user's response.

Embodiments of the present invention recognize that augmented reality sound enables augmentation of sound detected by a user in response to exposure of the user to a stimulus of detected sounds, objects, or both. Embodiments of the present invention provide a method for modifying a user response to visual and/or audio experience by augmenting the visual and/or audio experience of a user with alternative sounds determined to modify the user response by applying machine learning techniques, based on user feedback. Implementation of embodiments of the invention may take a variety of forms, and exemplary implementation details are discussed subsequently with reference to the Figures.

Embodiments of the present invention perform machine learning techniques to determine the user's response to detecting a sound, viewing a particular object, or a combination of both. Embodiments of the present invention additionally determine a user's response to an object that does not emanate sound, as well as a non-sound emitting object that is associated with a non-natural sound. Embodiments of the present invention utilize machine learning techniques in order to determine and store a user's response to a given stimulus.

In some embodiments, supervised machine learning, using classification and regression based models are used to determine a user's response to a particular sound emanating from, or associated with, a particular source, such as an object. For example, each iteration of supervised machine learning utilizes one or a combination of inputs, such as a sound, an object, or a sound and an object, which act as a "vector," and triggers a response output, which is a "supervisory signal." Iterations of supervised machine learning typically compare the supervisory signal data to a set of training data, which is a set of baseline data, defining the characteristics of the category in which the machine learning outputs belong. The supervised machine learning determines the category in which the machine learning outputs are assigned. Categories to which machine learning outputs are assigned include: fear, anger, sadness, joy, disgust, trust, anticipation, or surprise. Supervised machine learning techniques utilized by embodiments of the present invention may include: linear regression, random forest, and support vector machines. Additionally, embodiments of the present invention may utilize the following techniques: (i) determining the type of training examples; (ii) gathering a training set; (iii) determining the input feature representation of the learned function; (iv) determining the structure of the learned function and corresponding learning algorithm; (v) running the learning algorithm on the gathered training set; and (vi) evaluating the accuracy of the learned function.

Embodiments of the present invention recognize and record natural and non-natural sounds. Natural sounds are sounds that are part of a non-computer generated soundscape, which is a component of an acoustic environment that can be perceived by a user's hearing, or sounds having frequencies that are not necessarily perceived by a user's hearing. Natural sounds include, but are not limited to "ambient sounds", which are background sounds including mechanical sources, and living organisms. Natural sounds also include those generated by natural, non-biological sources, such as earth, wind, fire, and water. Non-natural sounds are sounds that are included in a computer-generated soundscape, which is a component of a non-natural acoustic environment, as well as those sounds that are used to augment the natural sounds perceived by the user. Non-natural sounds include any sound recorded or generated into a digitized file, such as one of the following file formats in the following non-exhaustive list: (i) Multi-Image Network Graphics (.mng), (ii) Audio Video Interleave (.avi), (iii) QuickTime File Format (.mov, .qt), (iv) Windows Media Video (.wmv),(v) Compact Disc Read-Only Memory (CD-ROM), (vi) Digital Versatile Disc Read-Only Memory (DVD-ROM), (vii) Blu-Ray Disc, (viii) High Definition Digital Versatile Disc (HD DVD), (ix) Matroska Multimedia Container (.mkv), (x) MPEG-1 and/or MPEG-2 Audio Layer III (.mp3), (xi) MPEG-4 Part 14 (.mp4), or other video or audio file format now known or later conceived.

Although some portions of this document speak in terms of matching objects, this is a bit of a misnomer. In many embodiments of the present invention, real world objects (detected in images captured by the AR imaging hardware) are matched (or at least checked for matches) against categories of objects by machine logic rules. The following list of example embodiments will help make this concept of "categories of objects" more clear: (i) objects that correspond to a human body covered more than 75% in bandages and in in a standing position will match the "mummy category" and will trigger the following audio: "beware the curse of the mummy;" (ii) objects that correspond to electric cars, which are in motion relative to the AR user and are not in the AR user's current field of vision will be placed in the category called "Potentially Unknown Quiet Vehicle" and will trigger the AR system to amplify sound frequencies most strongly associated with the operation of electric cars; (iii) a softball sized and shaped object that is heading toward the user at a slow speed matches the category "Slow Pitch Softball" and triggers the following audio: "ssllloooooow-www pitch . . . wait . . . for . . . it;" (iv) a vertical streak of light (which can be considered an "object" as that term is used herein because it is visible in the manner that a solid or liquid object is visible to a person) is placed in the category "Lightning" and causes a temporary masking of all sounds to the user (which in this case happens to be a dog who is very afraid of thunder); (v) an object is that bears a universal product code (that is, a UPC) which is unique to a user is placed in the category "My Stuff" and triggers the following audio: "there is your stuff;" and (vi) an object determined to be likely to be a consumer product made by the ABC Manufacturing Company is placed is the category "Our Competitor's Shoddy Products" and this category match, when coupled with detection of a frustrated look on the face of the AR user, triggers the following audio: "the XYZ Manufacturing Company makes great quality consumer products that make our customers super happy despite the premium prices we charge in exchange for this extra margin of quality! Hooray for XYZ! The Happy-Maker!"

As will be apparent to those of skill in the art, the matching of an object into a category of objects, by machine logic based rules, will depend upon whether the object in the AR image(s) meets certain conditions. A non-exhaustive list of possible types of conditions follows: (i) size and shape of object; (ii) brightness of object; (iii) color of object; (iv) reflectiveness of object; (v) surface characteristics (for example, smoothness, color, combination of colors, texture) of object; (vi) distance or position of object relative to AR user; (vii) speed of object (absolute or relative (for example, relative to AR user)) (viii) direction of movement of object (absolute or relative); (ix) changes in size and shape of object (for example, size and shape changes indicating that the object is breathing); and/or (x) symbolic meaning of human or machine readable symbols (such as, trademarks, UPC symbols, speed limit signs, etc.).

III. Embodiments of the Present Invention

The present invention will now be described in detail with reference to the Figures. FIG. 1 is a functional block diagram illustrating a distributed computer processing environment, generally designated as 100, in accordance with an embodiment of the present invention. Distributed computer processing environment 100 includes: AR Headset 115, mobile device 120, server 125, and repository 130, all interconnected via network 135. Distributed computer processing environment 100 further contains object 105, sound input 110, and biometric sensor 140. Server 125 includes machine learning program 300, and is communicatively connected to biometric sensor 140. AR Headset 115 contains sound association program 400. The term "distributed" as used in this specification describes a computer system that includes multiple, physically distinct devices that operate together as a single computer system. FIG. 1 provides only an illustration of one implementation and does not imply any limitations with regard to the environments in which different embodiments may be implemented. Many modifications to the depicted environment may be made by those skilled in the art without departing from the scope of the invention as recited by the claims.

Object 105 is a visible, physical article or a representation of a physical article that is recorded on a tangible medium of expression. In some embodiments, object 105 may include physical articles such as: chairs, floors, walls, television sets, computers, computer screens, persons, vehicles, plants, animals, telephones, wires, and papers. In some embodiments, object 105 may also include movable and non-movable images on a television or computer screen, where the "images" can include representations of physical objects, such as those mentioned above as "physical articles." For example, if a user is looking at a television screen depicting a forest, the visual representation of the individual trees in the forest can collectively be considered as object 105, even though the individual trees are not physically a part of the user's immediate observable environment. In yet other embodiments, object 105 includes physical articles that do not emanate sound, such as an iron or a painting.

Sound input 110 is a sound that is either used as a basis for augmenting a user response to a stimulus or is used to augment a user experience. In some embodiments, sound input 110 can be natural sound emanating from object 105. In other embodiments, sound input 110 can include non-natural sounds with which object 105 is tagged. For example, if a user is observing an object in a park, such as a barking dog, the barking sound emanating from the dog can be considered as sound input 110. Additionally, if the user is observing an object that does not emit sound, such as an iron, a sound that is chosen by the user that the user may associate with the iron can similarly be considered as sound input 110.

AR Headset 115 is a physical device that is worn by a user. In some embodiments of the present invention, AR Headset 115 includes a wearable device designed to be removably attached to a user's head, and contains sound association program 400. In some embodiments AR headset 115 encompasses the user's eyes and ears. In some embodiments, AR Headset 115 is configured to contain a display that is designed to be utilized with AR Headset 115, such as a pair of glasses that provide information not readily available in the user's environment or a fully encompassing apparatus, such as a pair of goggles or a helmet, that provides information not readily available in the user's environment. For example, AR Headset 115 includes a headpiece worn by the user that enables the user to interact with his or her immediate environment, providing visual and audio input of the immediate environment, and provide augmentation of visual and/or audio input. AR headset 115 is discussed in more detail with regards to FIG. 2.

Mobile device 120 is a network communications device that can be communicatively connected to AR Headset 115, via network 135. In some embodiments of the present invention, a user selects from a menu of available options on mobile device 120 in order to provide feedback of the user's response to a stimulus. For example, if a user is in a living room environment and sees a chair while wearing AR Headset 115, mobile device 120 will prompt the user to select at least one option relevant to the relationship between the user and the chair. The options include responses from which the user can select, such as: fear, anger, sadness, joy, disgust, anticipation, surprise, or shame.

Server 125 is a computer that is configured to contain machine learning program 300. In some embodiments of the present invention, server 125 is a standalone computing device, a management server, a web server, a mobile computing device, or any other electronic device or computing system capable of receiving, sending, and processing data. In other embodiments, server 125 can represent a server computing system utilizing multiple computers as a server system, such as in a cloud computing environment. In another embodiment, server 125 may be a laptop computer, a tablet computer, a netbook computer, a personal computer (PC), a desktop computer, a personal digital assistant (PDA), or a smart phone. Embodiments of server 125 may include internal and external hardware components, as depicted and described in further detail with respect to FIG. 5.

Repository 130 is a data storage device that is connected to server 125, and is communicatively connected to AR Headset 115. In some embodiments, repository 130 includes various types of storage, such as a database, a database server, an online data storage, a digital file system, a physical file system, and/or a data warehouse. In some embodiments, repository 130 stores data associating objects and sounds to user responses. In some embodiments, repository 130 can be updated in real-time to reflect the changes in object/sound associations to user responses, as machine learning program 300 learns user responses to various sounds and objects. Repository 130 also includes stored data associating the effect of one stimulus/response association, on another stimulus/response association, based on machine learning. Subsequent to determining a user response to various applied stimuli, machine learning program 300 determines the effect of applying a second stimulus in response to a user's response to a first stimulus, thus determining whether the second stimulus mitigates, amplifies, or has no discernable effect on the user's response to the first stimulus.

Network 135 may be, in a non-limiting example, a local area network (LAN), a telecommunications network, a wide area network (WAN), such as the Internet, a virtual local area network (VLAN), a cable-broadcasting delivery network, a satellite broadcasting delivery network, or any combination of network types that can include wired, wireless, or optical connections. Network 135 can be any combination of connections and protocols that will support communications between AR Headset 115, mobile device 120, server 125, and repository 130, in accordance with embodiments of the present invention.

Biometric sensor 140 is a collection of one or more sensors that is designated to detect and measure the user's biometric information. In some embodiments of the present invention, the collection of sensors of biometric sensor 140 are arranged in an area in which a user is presented a stimulus, and the user's response in terms of the biometric measurements are received and associated with the particular stimulus. In other embodiments, biometric sensor 140 may be embedded in AR Headset 115 and is used to receive the biometric information being measured in response to a presented stimulus, such as an object, a sound, or combination of an object and its associated sound. For example, if a user is wearing AR Headset 115, and upon being exposed to an object in her immediate observable environment, the user's heartrate increases, then biometric sensor 140 can detect the increase in heartrate, where the increase corresponds to a characteristic of a response, and the heartrate corresponds to biometric information. In some embodiments, biometric information being measured by biometric sensor 140 includes: heartrate, breathing rate, voice tonality, skin conductivity levels, temperature, eye dilation, facial expression, iris and retinal recognition, audio response of the user, gait, and vein recognition. For example, upon a user observing a scary object in his immediate observable environment, biometric sensor 140 can determine the user's physiological response by detecting whether the user's heart rate increases, breathing deepens, and/or is beginning to sweat. Further, biometric sensor 140 can, for example, detect a user's unique voice and determine speech emitted, or whether that voice has been altered upon being exposed to an object, such as a user emitting a loud shriek.

Figure 2:
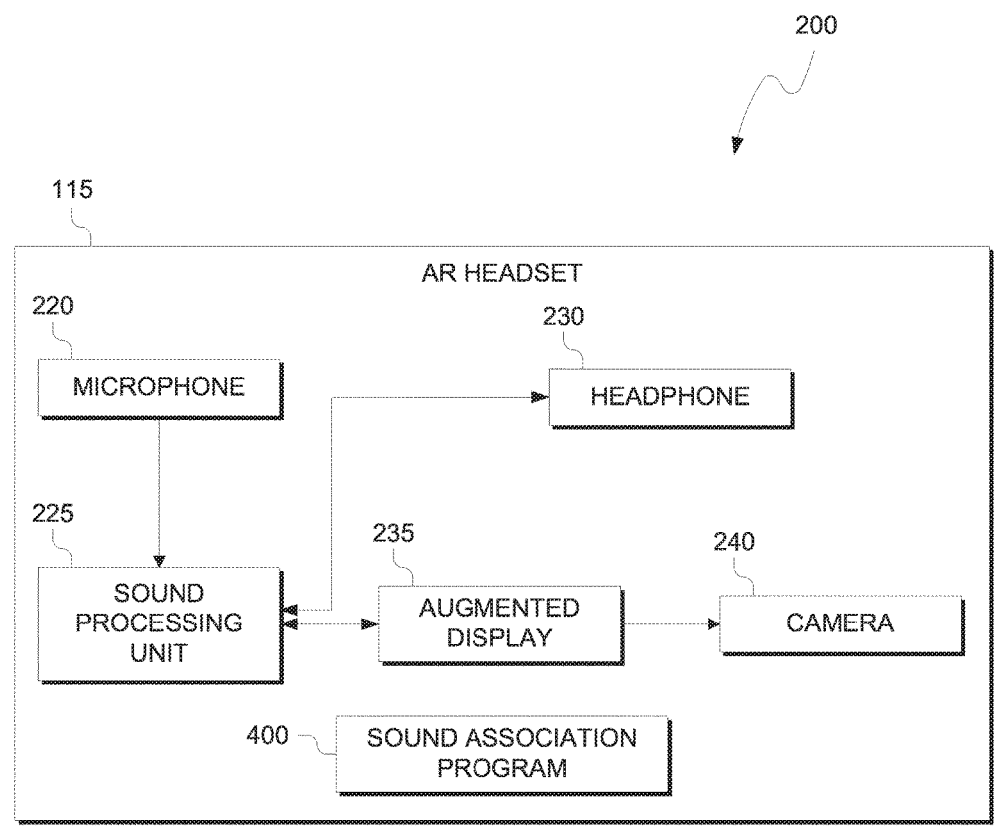
FIG. 2 is a functional block diagram illustrating an Augmented Reality Headset ("AR Headset") for determining a user response to sound associated with objects, within the distributed computer processing environment of FIG. 1, in accordance with an embodiment of the present invention.

FIG. 2 is a functional block diagram illustrating components of AR Headset 115, generally designated as 200, according to an embodiment of the present invention. AR Headset 115 contains: microphone 220, sound processing unit 225, headphone 230, augmented display 235, camera 240, and sound association program 400.

Microphone 220 is a device that is designed to receive sounds detected from a user's immediate environment. In some embodiments of the present invention, microphone 220 can be a directional microphone, which can detect and receive sounds coming from various directions with respect to the position of microphone 220. In other embodiments, microphone 220 can be a non-directional microphone, which detects and collects sounds from a specific direction based on the orientation of microphone 220. In some embodiments, microphone 220 may include filtering features to detect sounds of particular frequency ranges, or volume levels.

Sound processing unit 225 is a sound modification system that alters the characteristic of an input sound. In some embodiments, sound processing unit 225 includes a processor that can perform at least the following functions: increasing the decibel value of an input sound, reducing the decibel value of an input sound, maintaining the decibel value of an input sound, canceling an input sound, or replacing an input sound with an alternate sound. In some embodiments, sound processing unit 225 replaces an input sound with a non-natural sound stored in repository 130.

Headphone 230 is a sound delivery device that is attachable to at least one ear of the user, such that the user hears the delivered sound. In some embodiments, headphone 230 includes an earphone that directly transmits an audio signal to an ear of a user. For example, headphone 230 can be a wearable audio delivery device containing at least one ear cup or ear insert, and the ear cup or ear insert can deliver sound to the user. In some embodiments, headphone 230 can deliver either naturally occurring sounds from the user's immediate environment, reproduced sounds, or digitally generated sounds, to the user. For example, if a user observes a moving object that emanates sound, such as a character in a movie, the emanated sound can be delivered to the user via headphone 230.

Augmented display 235 is a type of visual display that is capable of displaying the images or video captured by camera 240. In some embodiments, augmented display 235 can be attached to AR Headset 115, such that augmented display 235 can produce a display of a realistic representation of a user's surrounding environment, replacing the real-world view. In other embodiments, a user can view real-world images and receive augmentation on top of or overlaid on the real-world images, by use of augmented display 235.

Camera 240 is an image capturing device for recording visual images in the form of a photograph or video signals. In some embodiments of the present invention, camera 240 may be one or a combination of camera types that includes a (an): action camera, animation camera, autofocus camera, backup camera, body camera, box camera, camera phone, closed-circuit television camera, canon camera, digital camera, field camera, helmet camera, light-field camera, multiplane camera, or any other type of camera that is now known or later created. In some embodiments, for example, camera 240 can be used to capture a live feed, or record and play a visual feed in order to establish the visual environment which AR Headset 115 will use to augment an interactive user experience.

In some embodiments, camera 240 can be used to determine a user's response to a given stimulus by associating facial expressions to the relevant emotion. For example, if a user is exposed to a scary character in a horror film, and the user's facial expression changes so as to express fear, camera 240 is enabled to capture the change in the user's facial expression. Further, for example, camera 240 can record facial micro-expressions, which can occur as fast as $1/15$ to $1/25$ of a second. Camera 240 can record at least the following micro-expressions: disgust, anger, fear, sadness, happiness, surprise, and contempt. The recording of the user micro-expressions by camera 240 is used to associate a user response to a given stimulus. In some embodiments, camera 240 is a collection of image capturing devices communicatively connected to AR Headset 115. For example, camera 240 can be a collection of wall-mountable cameras arranged so as to capture a 360-degree view of the user's immediate observable environment. In some embodiments, camera 240 is operationally connected to AR Headset 115, and captures still or moving images of the user's immediate observable environment.

Sound association program 400, contained in AR Headset 115, is a program used to deliver or modify an input sound that is transmitted to the user. In some embodiments, sound association program 400 receives a stimulus as its input, identifies the S/R association from the stimulus, determines whether there is an S/R association pair to provide a desirable modification to a user's response, and ultimately modifies the user response by applying a known S/R association as an input sound transmitted to the user. Embodiments of sound association program 400 will be discussed in further detail below with respect to FIG. 4.

Figure 3A:
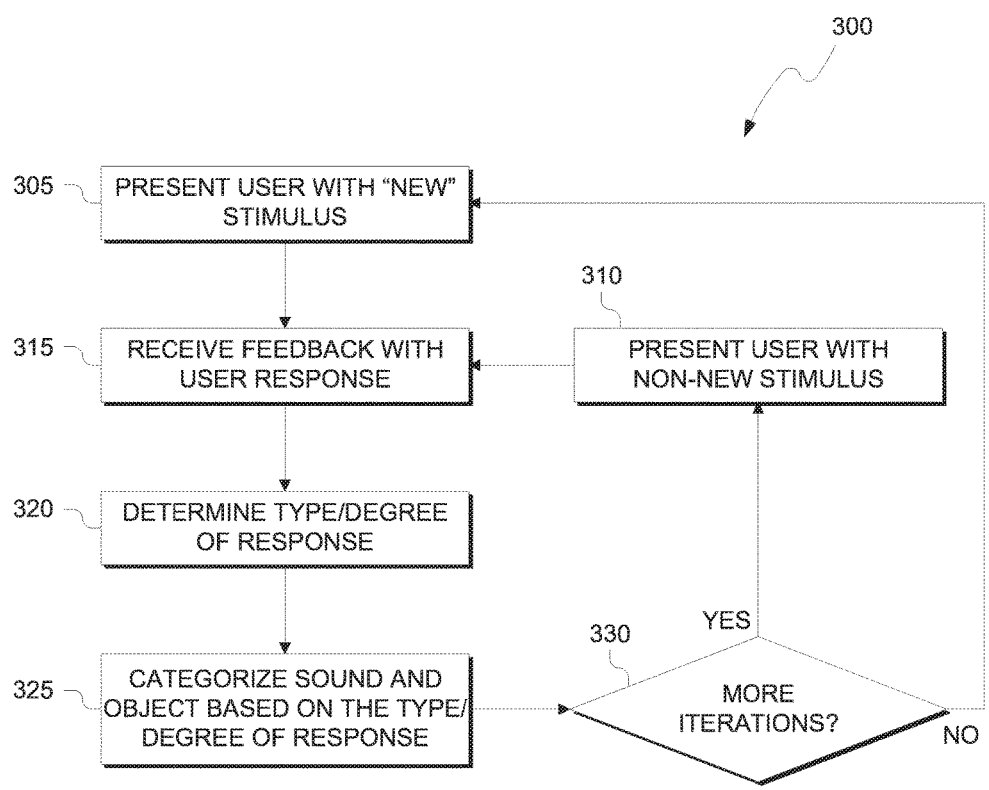
FIG. 3A illustrates operational steps of a machine learning program, operating on a client device, within the distributed computer processing environment of FIG. 1, in accordance with an embodiment of the present invention.

FIG. 3A is a flowchart illustrating operational steps of a machine learning program, generally designated as 300, within distributed computer processing environment 100, for learning a user's response to a particular sound, viewing an object, or a sound associated with an object, in accordance with an embodiment of the present invention.

In step 305, machine learning program 300 receives a "new stimulus." In some embodiments, the "new stimulus" is considered a stimulus presented to a user for the first time for machine learning purposes, whereas reference to a "non-new" stimulus indicates an iterative exposure of the stimulus to the user. For example, if a user is exposed to a cellular phone ringtone sound for the first time, the exposure to the cellular phone is considered a "new stimulus." If the user is exposed to a cellular phone ringtone sound for the second time, the exposure is now considered a "non-new stimulus." In some embodiments, microphone 220 receives sound input 110 from a user's immediate observable environment, where sound input 110 either emanates from object 105, or object 105 is given an association with a non-natural sound. For example, if a user is wearing AR Headset 115 and observes a stray cat that is purring in his immediate observable environment, and the sound of the purr is associated with the cat, then the purring cat is said to be a "stimulus" that machine learning program 300 presents to the user. Additionally, for example, if a user is wearing AR Headset 115 and observes a silent iron that is tagged with a non-natural sound, thereby becoming a non-silent iron, the non-silent iron and the non-natural sound tagged to the iron, is considered to be a "stimulus" that machine learning program 300 presents to the user.

In step 315, machine learning program 300 receives feedback from a user's response. In some embodiments, machine learning program 300 requires that the user manually select from a menu of populated responses. For example, in response to a given stimulus, the menu of populated responses can include a range of emotions, or states of mind, including: fear, anger, sadness, joy, disgust, trust, anticipation, surprise, shame, pity, indignation, envy, and love. In other embodiments, machine learning program 300 uses biometric feedback to determine the user's reaction to the given stimulus, and the responses determined include the emotions and states of mind that appear on the menu of populated responses presented to a user on mobile device 120, for example. In yet other embodiments, machine learning program 300 uses facial expression techniques, through use of camera 240, to determine the user's reaction to the given stimulus, and the reactions determined include the emotions and states of mind that appear on the menu of populated responses.

In step 320, machine learning program 300 determines the type and degree of the user response, where "type" refers to at least one emotion or state of mind referred to above, and "degree" refers to the extent or magnitude to which the user is experiencing a particular emotion or state of mind. In some embodiments, machine learning program 300 will determine the type and degree of the user response based on a user input, or a second user interpreting a user's response, which can be, for instance, selectable from a menu of populated responses. In some embodiments, the user input will be subjective in nature, and the consistency with which the user inputs a user response will be indicative of the accuracy of a future suggestion by machine learning program 300. For example, if a user is feeling slightly fearful upon being exposed to a given stimulus, the user can inform machine learning program 300 of two pieces of information: (1) that the user is feeling "fearful," and (2) that the user is fearful to a minimal extent. If the user is consistently feeling "slightly fearful" when exposed to a given stimulus, then machine learning program 300 will assume that: (i) the user's fear is to a minimal extent, and (ii) the user's fear level will not rise above the assumed minimal extent. In some embodiments, machine learning program 300 can determine the "degree" of the user response by prompting the user to select a value on a scale having a minimum and maximum value, and assessing the value relative to the minimum and maximum values. For the case in which machine learning program 300 cannot determine the user's emotional response based on biometric data, some embodiments of machine learning program 300 will manually prompt a user to select the degree of a user response on a scale of one through ten, with one being a minimum value and ten being a maximum value.

In other embodiments of the present invention, machine learning program 300 can determine the type and degree of a user response based on biometric feedback. For example, if a reading from biometric sensor 140 indicates that the user is experiencing a heartrate that is significantly higher than his baseline heartrate, along with a combination of other biometric feedback, then the "type" of the user response can be considered fear or excitement, while the "degree" of the user response may depend on the magnitude of the biometric response(s). If the measured heartrate is greater than the baseline by a significant measurement value, then the "degree" of the response may be said to be a "high degree." In some embodiments, machine learning program 300 calibrates the measured biometric data in order to ensure that the type and degree of the user response is accurate. For example, machine learning program 300 can determine various baseline biometric information, such as a resting heartrate or breathing rate. Machine learning program 300 can then compare the measured baseline biometric information and compare the information to a value(s) known in the scientific literature.

In some embodiments of the present invention, machine learning program 300 compares the collective biometric data of the user's response to a pre-existing repository of biometric data associated with emotional and state-of-mind responses. Machine learning program 300 selects the response that most closely matches the biometric data of the user's response, and associates the matched response from the pre-existing repository (not shown), with the stimulus as the type of response.

In step 325, machine learning program 300 categorizes a given stimulus based on the type and degree of the user response. In some embodiments, machine learning program 300 tags a given stimulus with the type and degree of the user response, which allows machine learning program 300 to associate a user response to a particular stimulus in order to form an S/R association. For example, if a user response indicates that he is slightly fearful upon seeing a hissing cat, machine learning program 300 will tag the hissing cat with the information that the user is slightly fearful upon observing the hissing cat. In response to categorizing the given stimulus to the type and degree of the user response, machine learning program will proceed to step 330.

In decision step 330, machine learning program 300 determines if more iterations need to occur for a particular stimulus. In the case in which machine learning program 300 determines that more iterations need to occur (step 330, "YES" branch), sound association program 300 proceeds to step 310. In step 310, machine learning program 300 presents a user with a "non-new" stimulus. In some embodiments of the present invention, the "non-new" stimulus is detection of a sound, or viewing of an object, which includes sound input 110, object 105, or a sound associated with object 105.

In the case in which machine learning program 300 determines that more iterations do not need to occur (step 330, "NO" branch), sound association program 300 proceeds to step 305 and presents the user with a "new" stimulus, and proceeds as described above. The reader will recognize that the decision to present additional iterations of a stimulus may not be in immediate succession, but may be repeated after other stimuli are presented, or may be presented at a subsequent time.

Figure 3B:
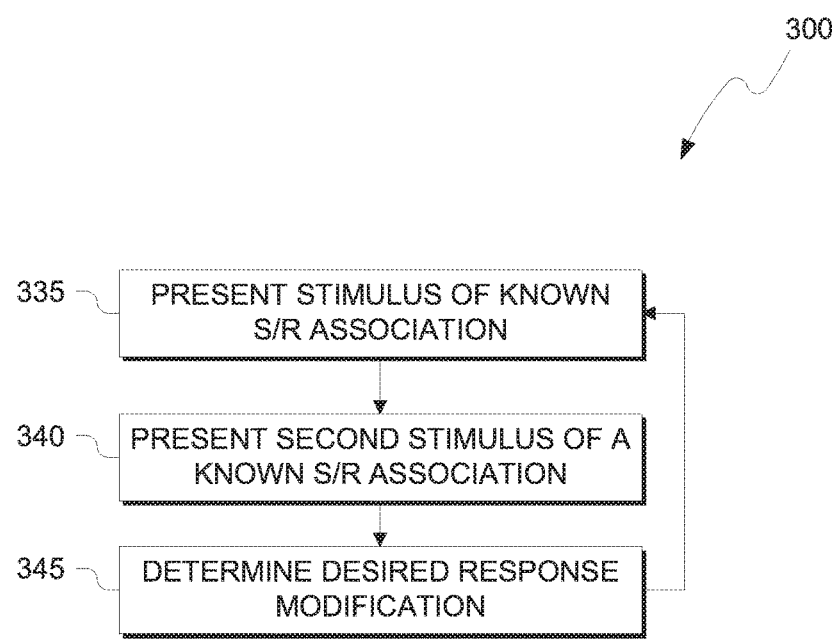
FIG. 3B illustrates additional operational steps of a machine learning program, operating on a client device, within the distributed computer processing environment of FIG. 1, in accordance with an embodiment of the present invention.

FIG. 3B is a flowchart illustrating additional operational steps of machine learning program 300, within distributed computer processing environment 100, for determining the effect of applying a second S/R association to a user presented with a first S/R association; the two S/R associations form an S/R pairing, in accordance with an embodiment of the present invention.

In step 335, machine learning program 300 presents a stimulus of a first S/R association of a plurality of known S/R associations to the user. In some embodiments, the plurality of known S/R associations can be represented from a first S/R association (S1/R1) to an "nth" S/R association (Sn/Rn). Machine learning program 300 presents the first S/R association to the user. For example, if machine learning program 300 determines the user response to hearing thunder is fear (as determined by machine learning program 300 in FIG. 3A), machine learning program 300 presents a sound of thunder to the user, and the user exhibits the known response of fear.

In step 340, machine learning program 300, having presented a first S/R association to the user, presents a second stimulus of a second S/R association to the user. In some embodiments, for a plurality of S/R associations, from 1 to 'n', machine learning program 300 applies the stimulus of S1/R1 association to the user, and responsive to the user's response to S1, machine learning program 300 applies the stimulus (S2) of a second S2/R2 association, in which S2/R2 is one of the plurality of S/R associations determined by machine learning program 300 as described in discussion of FIG. 3A. For example, machine learning program 300 applies the sound of thunder to the user, who exhibits a response of fear, as part of a known S/R association. Machine learning program 300, in response to the user's response of fear to hearing the sound of thunder, presents a second stimulus of the sound of laughter (S2), for example, a sound which is known to calm the user and make the user feel happy (R2). Machine learning program 300 applies S2 after presenting S1 to generate a pairing (S1/R1)–(S2/R2).

In step 345, machine learning program 300 determines the desired response modification. In some embodiments, machine learning program 300 determines the response modification based on the comparison of an initial user response of S1, and the response of the user after presenting S2. In some embodiments, machine learning program 300 selects a second S/R association based on previously establishing the type or category of the response of the second S/R association, and input by the user as to the relationship between the established categories of responses, as well as the user's desired direction and/or magnitude of the response modification. For example, if Si is a stimulus that causes a user response of fear (R1), and S2 is a stimulus that causes a user response of joy (R2), then when the user is exposed to S1, machine learning program 300, based on input of category relationship and user input of desired response modification, determines that the desired modification to the "fear" response is the application of the known response in the S/R pair, which in this case is R2—a "joy" response. Upon determining the desired response modification, machine learning program 300 will proceed to step 335 and continue until the effect on a user's response of the combinations of the previously established S/R associations are determined, and the pairings of S/R associations that modify the user's response in a preferred way are determined. In some embodiments of the present invention, the preferred modification is determined by the comparison of biometric data before and after the presentation of the second stimulus for the pairings of S/R associations. In other embodiments, the preferred modification is input by the user, for example, by use of mobile device 120.

Figure 4:
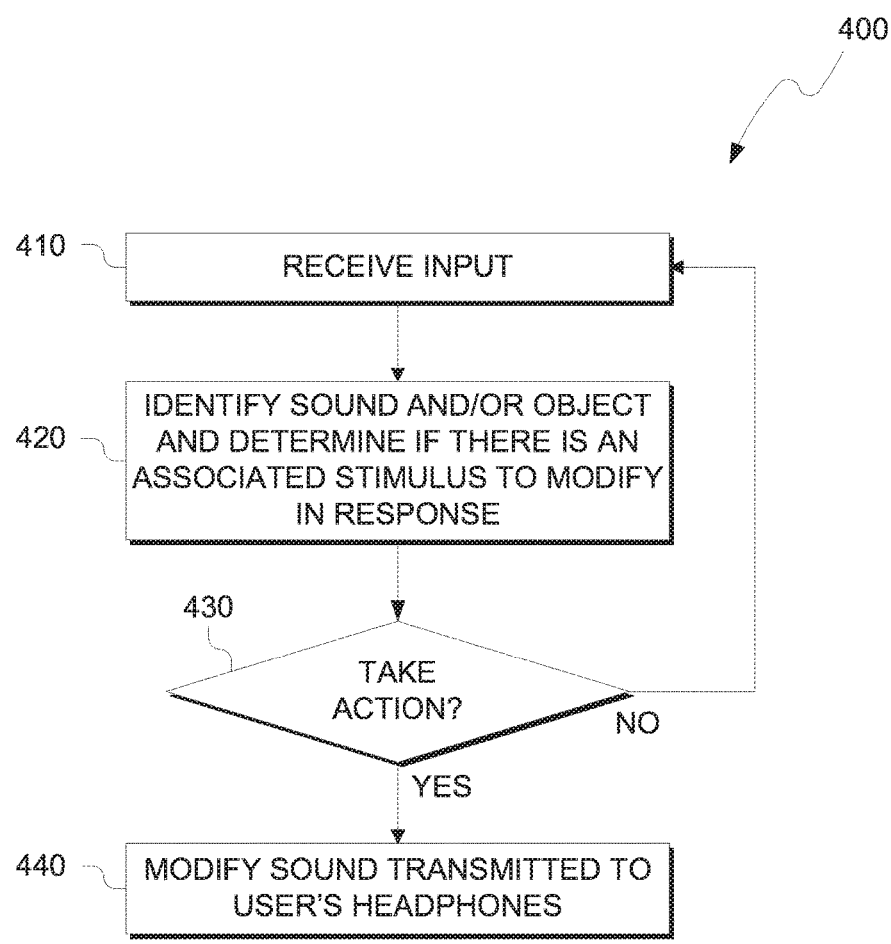
FIG. 4 illustrates operational steps of a sound association program, operating on a client device, within the distributed computer processing environment of FIG. 1, in accordance with an embodiment of the present invention.

FIG. 4 is a flowchart illustrating the operational steps of sound association program 400 within distributed computer processing environment 100, to provide a desired modification to an initial response, in accordance with an embodiment of the present invention. Embodiments of the present invention recognize that the operational steps of sound association program 400 are not necessarily presented in order, and may, when necessary, be performed out of order for purposes of logical coherency.

In step 410, sound association program 400 receives an input of natural sound, non-natural sound, or any combination of natural and non-natural sound, that is associated with a physical object or a representation of the physical object. For example, any sound that can be heard, however faintly, is a type of natural or non-natural sound that would constitute an input of natural or non-natural sound that sound association program 400 receives. In some embodiments, the natural sound can emanate from object 105. In some embodiments, the input of sound associated to an object, such as sound input 110 and object 105, can be received by sound association program 400 via camera 240, which is operationally attached to AR Headset 115. In some embodiments, sound association program 400 receives sound via microphone 220, which is operationally connected to AR Headset 115. In some embodiments, sound association program 400 receives a sound input before receiving a visual input. For example, if a user is wearing AR Headset 115 and sees lightning in his immediate observable environment for the first time, sound association program 400 may not be able to associate the lightning with a natural or non-natural sound, until the inevitable input of thunder is received moments later.

In some embodiments, sound association program 400 receives an input of a physical object or a representation of a physical object that is fixed on a tangible medium of expression ("input object"). For example, if an object is present in the user's immediate observable environment, and is detected by the user (as described below), then the object becomes an input object that is received by sound association program 400.

In step 420, sound association program 400 identifies a stimulus of either an input of a natural or non-natural sound ("input sound") or viewing of an object, and determines if there is a known S/R association for the stimulus and whether there is a second S/R association of a S/R pair to modify a user response. In some embodiments, sound association program 400 identifies the input sound and the source of the input sound. In some embodiments, the source of the input sound can be in the form a physical object or a representation of a physical object that can be viewed in at least one dimension. In some embodiments, sound association program 400 identifies the source of an input sound through the use of camera 240 or augmented display 235. In yet other embodiments, sound association program 400, using microphone 220, can detect the direction from which a particular natural sound is emanating, and assume that the ambient sound is coming from the same direction as the selected object. For example, if the purring cat appears in the user's immediate observable environment, upon detecting the cat as an "object," sound association program 400 will assume that because the purring sound is coming from the same direction as the cat, that the purring sound should be associated with the cat.

In some embodiments, sound association program 400 can identify an object first before detecting a natural or non-natural sound emanating from that object. For example, if a user sees an object that does not immediately emanate a sound, and that might cause a user response, such as lightning, sound association program 400 can still identify and store information regarding the identified object.

In decision step 430, sound association program 400 determines whether or not to perform a proscribed action. In the case in which sound association program 400 determines that a proscribed action is to be performed (step 430, "YES" branch), sound association program 400 proceeds to step 440 and modifies a sound transmitted to a user's headphones. In some embodiments, sound association program 400 will determine whether to perform a proscribed action based on determining if the stimulus detected is one of an S/R pair, for which a second stimulus has been determined to modify the initial user response in a preferred manner. Previous user input indicating whether the performance of an action is available to modify the initial response can come in the form of manually entered instructions on mobile device 120 or through verbal instructions to AR Headset 115 via microphone 220.

In step 440, sound association program 400 modifies the input sound and transmits the newly modified input sound to headphone 230. In some embodiments, sound association program 400 modifies the input sound by: increasing, decreasing, maintaining, silencing, or replacing the input sound. In some embodiments, sound association program 400 modifies the input sound to headphone 230 in order to elevate, maintain, or reduce an emotional response of a user when the user is exposed to a given stimulus. For example, if a user is watching a horror film, and a main character greatly frightens the user, sound association program 400, via machine learning program 300, can increase the input sound of the main character to elevate the user's fear. Further, if a user is walking down a poorly lit street at night, and hears footsteps approaching, the user can increase the sound of the oncoming footsteps in order to be more alert of his surroundings. Returning to the example of a user observing lightning from his living room, some embodiments of sound association program 400 can either associate a sound to the lightning, or recognize a sound pattern that results from observing the lightning, where lightning is the object that is identified. For example, if a user observes a flash of lightning, and this observation causes him fear, sound association program 400 can: (1) begin to play a non-natural sound that relates to "happy" or "calm" emotions immediately upon observing the lightning, or (2) wait 3-5 seconds and mask the sound of the resulting thunder by silencing, decreasing, or replacing the sound of the resulting thunder.

Returning to the case in which sound association program 400 determines that a proscribed action does not need to be performed (step 430, "NO" branch), sound association program 400 proceeds to step 410.

Figure 5:
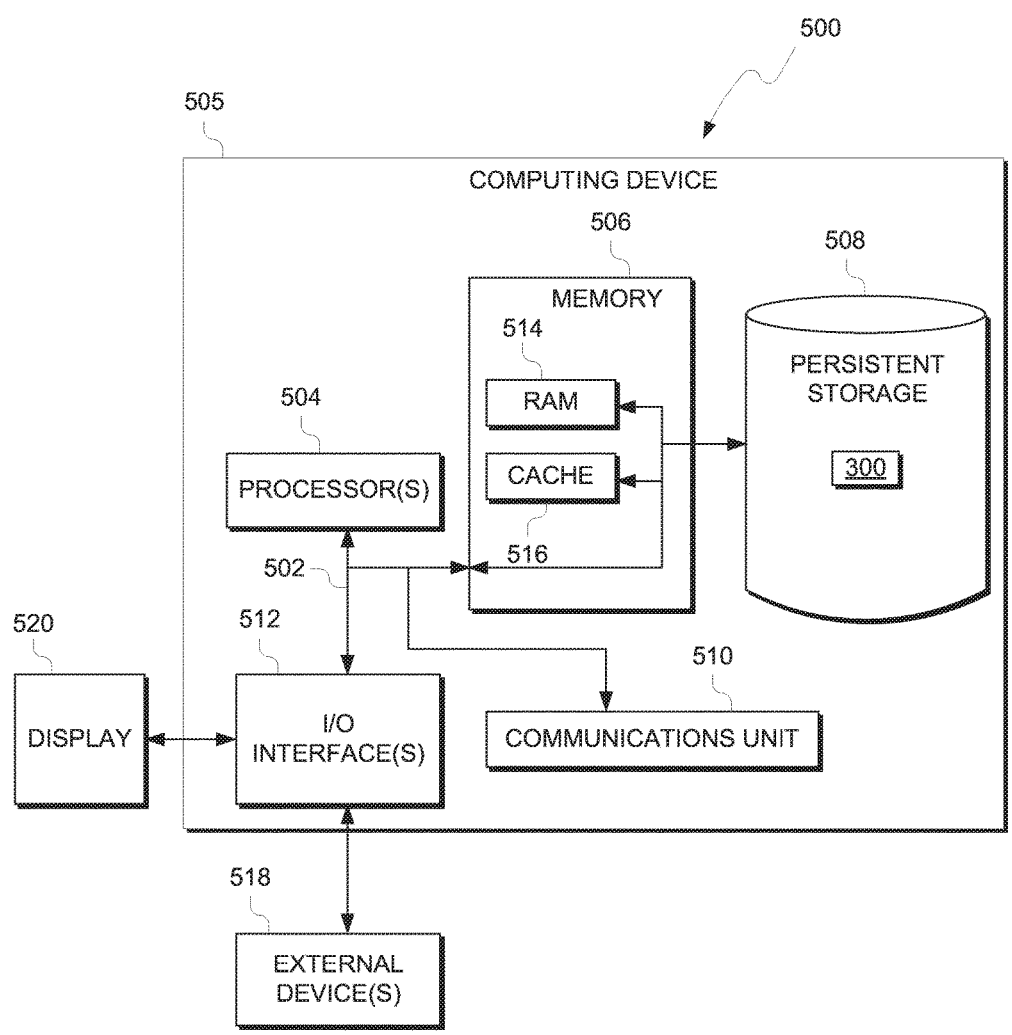
FIG. 5 depicts a block diagram of components of the server computer executing the intelligent mapping program within the distributed data processing environment of FIG. 1, in accordance with an embodiment of the present invention.

FIG. 5 depicts a block diagram of components of computer system 500, including computing device 505, having computer processing components similar to those of server 125 and AR headset 115, within distributed computer processing environment 100 of FIG. 1, in accordance with an embodiment of the present invention. Computing device 505 is capable of executing machine learning program 300, and sound association program 400, in accordance with an embodiment of the present invention. It should be appreciated that FIG. 5 provides only an illustration of one implementation and does not imply any limitations with regard to the environments in which different embodiments may be implemented. Many modifications to the depicted environment may be made.

Computer system 500 includes communications fabric 502, which provides communications between computer processor(s) 504, memory 506, persistent storage 508, communications unit 510, and input/output (I/O) interface(s) 512. Communications fabric 502 can be implemented with any architecture designed for passing data and/or control information between processors (such as microprocessors, communications and network processors, etc.), system memory, peripheral devices, and any other hardware components within a system. For example, communications fabric 502 can be implemented with one or more buses.

Memory 506 and persistent storage 508 are computer-readable storage media. In this embodiment, memory 506 includes random access memory (RAM) 514 and cache memory 516. In general, memory 506 can include any suitable volatile or non-volatile computer-readable storage media.

Machine learning program 300, and sound association program 400 are stored in persistent storage 508 for execution by one or more of the respective computer processors 504 via one or more memories of memory 506. In this embodiment, persistent storage 508 includes a magnetic hard disk drive. Alternatively, or in addition to a magnetic hard disk drive, persistent storage 508 can include a solid state hard drive, a semiconductor storage device, read-only memory (ROM), erasable programmable read-only memory (EPROM), flash memory, or any other computer-readable storage media that is capable of storing program instructions or digital information.

The media used by persistent storage 508 may also be removable. For example, a removable hard drive may be used for persistent storage 508. Other examples include optical and magnetic disks, thumb drives, and smart cards that are inserted into a drive for transfer onto another computer-readable storage medium that is also part of persistent storage 508.

Communications unit 510, in these examples, provides for communications with other data processing systems or devices, including resources of distributed computer processing environment 100. In these examples, communications unit 510 includes one or more network interface cards. Communications unit 510 may provide communications through the use of either or both physical and wireless communications links. Machine learning program 300, and sound association program 400 may be downloaded to persistent storage 508 through communications unit 510.

I/O interface(s) 512 allows for input and output of data with other devices that may be connected to computing device 505. For example, I/O interface 512 may provide a connection to external devices 518 such as a keyboard, keypad, a touch screen, and/or some other suitable input device (not shown). External devices 518 can also include portable computer-readable storage media such as, for example, thumb drives, portable optical or magnetic disks, and memory cards. Software and data used to practice embodiments of the present invention, e.g., machine learning program 300, and sound association program 400 can be stored on such portable computer-readable storage media and can be loaded onto persistent storage 508 via I/O interface(s) 512. I/O interface(s) 512 also connect to a display 520.

Display 520 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be any tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, a special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, a segment, or a portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method comprising:
   receiving, by an augmented reality system, a series of images corresponding to views of the real world;
   processing, by the augmented reality system, the series of images to determine presence of a first object;
   determining, by the augmented reality system, that the first object meets a first set of conditions such that the first object belongs to a first object category;
   responsive to the determination that the first object belongs to the first object category, providing an audio response in the form at least one of the following types of audio responses:
   communicating a predefined sound to an augmented reality user and/or changing audio characteristic(s) of a sound not generated by the augmented reality system which is being experienced by the augmented reality user;
   determining the augmented reality user's emotional reaction to seeing a second object; and
   defining the first object category and its associated first set of conditions by machine learning based, at least in part, on the emotional reaction that the augmented reality user had to the second object such that the second object belongs to the first object category.

2. The method of claim 1 wherein the determination of the augmented reality user's emotional reaction includes:
   receiving a set of machine logic based biometric feedback rules that correlate biofeedback patterns with emotional reactions;
   monitoring, by biofeedback hardware, the augmented reality user to obtain a first biofeedback pattern, with the monitoring occurring while the augmented reality user is seeing the second object; and
   applying the set of machine logic based biometric feedback rules to first biofeedback pattern to determine the augmented reality user's emotional reaction to seeing the second object.

3. The method of claim 1 wherein the determination of the augmented reality user's emotional reaction includes:
   receiving a set of machine logic based facial expression rules that correlate facial expression patterns with emotional reactions;
   capturing a set of image(s), by facial imaging hardware, of the augmented reality user's face, with the image capture occurring while the augmented reality user is seeing the second object;
   processing, by machine logic, the set of image(s) to obtain a first facial expression pattern; and
   applying the set of machine logic based facial expression rules to first facial expression pattern to determine the augmented reality user's emotional reaction to seeing the second object.

4. The method of claim 1 wherein the determination of the augmented reality user's emotional reaction includes receiving user input data including information indicative of the augmented reality user's emotional reaction to the second object.

5. A computer program product comprising:
   a machine readable storage device including a storage medium; and
   computer code stored on the storage medium of machine readable storage device, with the computer code including instructions for causing a processor(s) set to perform operations including the following:
   receiving, by an augmented reality system, a series of images corresponding to views of the real world,
   processing, by the augmented reality system, the series of images to determine presence of a first object,
   determining, by the augmented reality system, that the first object meets a first set of conditions such that the first object belongs to a first object category,
   responsive to the determination that the first object belongs to the first object category, providing an audio response in the form of one at least one of the following types of audio responses: communicating a predefined sound to an augmented reality user and/or changing audio characteristic(s) of a sound not generated by the augmented reality system which is being experienced by the augmented reality user,
   determining the augmented reality user's emotional reaction to seeing a second object, and
   defining the first object category and its associated first set of conditions by machine learning based, at least in part, on the emotional reaction that the augmented reality user had to the second object such that the second object belongs to the first object category.

6. The computer program product of claim 5 wherein the determination of the augmented reality user's emotional reaction includes:
   receiving a set of machine logic based biometric feedback rules that correlate biofeedback patterns with emotional reactions;
   monitoring, by biofeedback hardware, the augmented reality user to obtain a first biofeedback pattern, with the monitoring occurring while the augmented reality user is seeing the second object; and
   applying the set of machine logic based biometric feedback rules to first biofeedback pattern to determine the augmented reality user's emotional reaction to seeing the second object.

7. The computer program product of claim 5 wherein the determination of the augmented reality user's emotional reaction includes:
  receiving a set of machine logic based facial expression rules that correlate facial expression patterns with emotional reactions;
  capturing a set of image(s), by facial imaging hardware, of the augmented reality user's face, with the image capture occurring while the augmented reality user is seeing the second object;
  processing, by machine logic, the set of image(s) to obtain a first facial expression pattern; and
  applying the set of machine logic based facial expression rules to first facial expression pattern to determine the augmented reality user's emotional reaction to seeing the second object.

8. The computer program product of claim 5 wherein the determination of the augmented reality user's emotional reaction includes receiving user input data including information indicative of the augmented reality user's emotional reaction to the second object.

9. A computer system comprising:
  a processor(s) set;
  a machine readable storage device; and
  computer code stored on the machine readable storage device, with the computer code including instructions for causing the processor(s) set to perform operations including the following:
    receiving, by an augmented reality system, a series of images corresponding to views of the real world,
    processing, by the augmented reality system, the series of images to determine presence of a first object,
    determining, by the augmented reality system, that the first object meets a first set of conditions such that the first object belongs to a first object category,
  responsive to the determination that the first object belongs to the first object category, providing an audio response in the form of one at least one of the following types of audio responses: communicating a predefined sound to an augmented reality user and/or changing audio characteristic(s) of a sound not generated by the augmented reality system which is being experienced by the augmented reality user,
    determining the augmented reality user's emotional reaction to seeing a second object, and
    defining the first object category and its associated first set of conditions by machine learning based, at least in part, on the emotional reaction that the augmented reality user had to the second object such that the second object belongs to the first object category.

10. The computer system of claim 9 wherein the determination of the augmented reality user's emotional reaction includes:
  receiving a set of machine logic based biometric feedback rules that correlate biofeedback patterns with emotional reactions;
  monitoring, by biofeedback hardware, the augmented reality user to obtain a first biofeedback pattern, with the monitoring occurring while the augmented reality user is seeing the second object; and
  applying the set of machine logic based biometric feedback rules to first biofeedback pattern to determine the augmented reality user's emotional reaction to seeing the second object.

11. The computer system of claim 9 wherein the determination of the augmented reality user's emotional reaction includes:
  receiving a set of machine logic based facial expression rules that correlate facial expression patterns with emotional reactions;
  capturing a set of image(s), by facial imaging hardware, of the augmented reality user's face, with the image capture occurring while the augmented reality user is seeing the second object;
  processing, by machine logic, the set of image(s) to obtain a first facial expression pattern; and
  applying the set of machine logic based facial expression rules to first facial expression pattern to determine the augmented reality user's emotional reaction to seeing the second object.

12. The computer system of claim 9 wherein the determination of the augmented reality user's emotional reaction includes receiving user input data including information indicative of the augmented reality user's emotional reaction to the second object.

* * * * *